United States Patent [19]

Ono et al.

[11] 4,157,348

[45] Jun. 5, 1979

[54] PROCESS FOR PREPARING GUANIDINE

[75] Inventors: Hiroshi Ono, Fujisawa; Shigeru Inoue, Kamakura, both of Japan

[73] Assignee: Mitsui Toatsu Chemicals, Inc., Tokyo, Japan

[21] Appl. No.: 888,613

[22] Filed: Mar. 21, 1978

[30] Foreign Application Priority Data

Apr. 5, 1977 [JP] Japan .................................. 52/38093

[51] Int. Cl.$^2$ ......................................... C07C 129/00
[52] U.S. Cl. ................................................. 260/564 D
[58] Field of Search ..................................... 260/564 D

[56] References Cited

U.S. PATENT DOCUMENTS 3,952,057  4/1976  Schmidt et al. ................. 260/564 D

FOREIGN PATENT DOCUMENTS 9572762  7/1962  Japan ................................... 260/564 D

*Primary Examiner*—Gerald A. Schwartz
*Attorney, Agent, or Firm*—Fisher, Christen and Sabol

[57] ABSTRACT

A process is described for preparing guanidine by separating guanidine from a process stream obtained in a urea synthesis process, wherein ammonia and carbon dioxide are reacted at a high temperature and a high pressure. The process stream includes a urea synthesis effluent from a urea synthesis zone, a solution obtained by separating unreacted materials from the effluent, a concentrate of the solution or a mother liquor derived from a urea crystallization zone.

19 Claims, 1 Drawing Figure

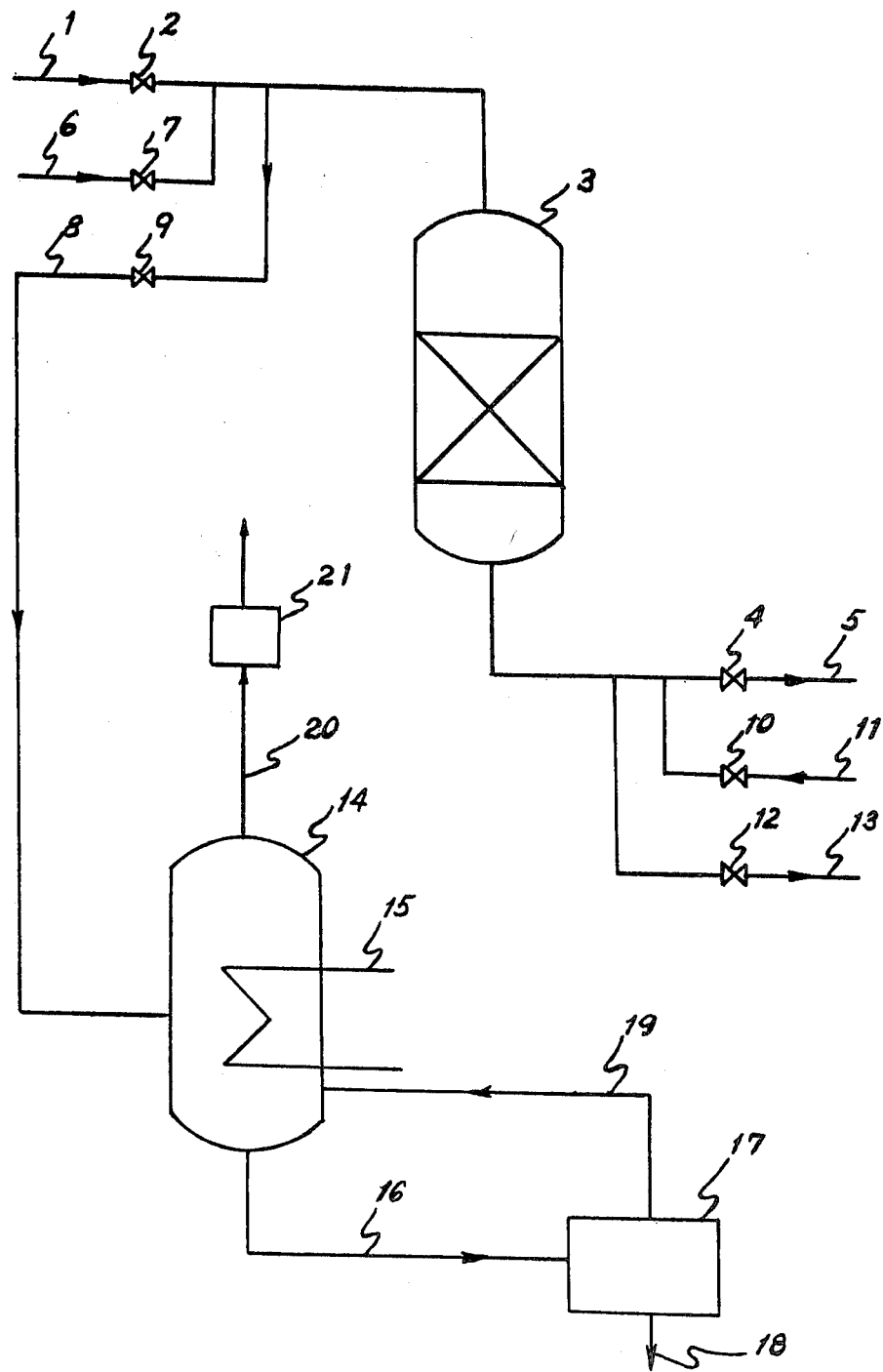

PROCESS FOR PREPARING GUANIDINE

BACKGROUND OF THE INVENTION

1. Field of the Invention

This invention relates to a process for preparing guanidine. The term "guanidine" used herein is intended to imply free guanidine, guanidine salts, and guanidine derivatives such as guanylurea and salts thereof. And if not specially described, the concentrations of guanidine described hereafter are the converted values as free guanidine.

2. Description of the Prior Art

In the industrial production of guanidine, guanidine is usually prepared from dicyandiamide and ammonium nitrate or other ammonium salts. In order to raise the efficiency of production, the production process must be conducted under high temperature conditions or under high temperature and high pressure conditions. When ammonium nitrate is used as a starting material and treated under such severe reaction conditions, there is a great danger of explosion.

SUMMARY OF THE INVENTION

It is accordingly an object of the present invention to provide a process for preparing guanidine which overcomes the above-stated disadvantages.

We have made a detailed study on the methods of synthesizing urea from ammonia and carbon dioxide and on the quality of the resultant urea. As a result, it has been found that in the synthesis of urea from ammonia and carbon dioxide a small amount of guanidine is always secondarily produced as a byproduct. It has also been found that the aqueous urea solution in any process stream in the zones downstream from the urea synthesis zone, inclusive of, such as a urea synthesis zone, an unreacted material separating zone wherein unreacted ammonia and ammonium carbamate are separated from a urea synthesis effluent, a zone for concentrating the aqueous urea solution, a urea crystallizing zone, or other zones contain several hundred to several thousand ppm of guanidine, calculated as free guanidine, on the basis of urea. We have made a further detailed study concerning guanidine based on the above findings and discovered that guanidine can be separated from the aqueous urea solution by the application of conventional unit operations.

According to the present invention, there is provided a process for preparing guanidine which comprises separating guanidine from a process stream in a urea production process wherein urea is prepared from ammonia and carbon dioxide.

BRIEF DESCRIPTION OF THE DRAWING

The sole FIGURE is a flow chart of a process for separating guanidine from a solution from a urea production process by an ion exchange method.

DETAILED DESCRIPTION OF THE PREFERRED EMBODIMENTS

In practice, the urea synthesis effluent is obtained by reacting ammonia, carbon dioxide and recovered ammonium carbamate in the urea synthesis zone operated at a temperature of 160°–250° C., preferably 170°–220° C. and most preferably 180°–200° C. and under a pressure of 80–400 kg/cm$^2$ (guage), preferably 140–350 kg/cm$^2$ (gauge) and most preferably 150–250 kg/cm$^2$ (gauge) with an NH$_3$/CO$_2$ mol ratio of 2.0–8.0, preferably 2.5–4.5 and an H$_2$O/CO$_2$ mol ratio of 0–2.0, preferably 0.2–1.5. The urea synthesis effluent is sent to the unreacted materials separating zone where substantially all of the unreacted ammonia and ammonium carbamate and part or all of the water formed in the urea synthesis reaction are separated from the urea synthesis effluent as a gaseous mixture of ammonia, carbon dioxide and water vapor. (The ammonium carbamate decomposes into carbon dioxide and ammonia). The separation is accomplished by a plurality of rectification or stripping stages using the same pressure as or a lower pressure than that used in the urea synthesis zone. The resulting aqueous urea solution may be directly concentrated to form a urea melt, which is then subjected to prilling. Alternatively, crystalline urea is separated from the concentrated urea solution in a crystallizer and then melted for prilling. The gaseous mixture of ammonia, carbon dioxide, and water vapor separated in the unreacted materials separating zone may be directly recycled to the urea synthesis zone as it is. Alternatively, the separated materials may be condensed or absorbed in water, an aqueous urea solution or an aqueous ammonium carbamate solution under the same pressure as the pressure in the unreacted material separation zone. The resulting absorbate is then recycled to the urea synthesis zone.

According to the process of the invention, guanidine is preferably separated from a process stream in the above-mentioned urea synthesis processes such as the urea synthesis effluent from the urea synthesis zone, the aqueous urea solution obtained by separating unreacted ammonia and ammonium carbamate from the urea synthesis effluent, a mother liquor obtained in the crystallizer after separation of crystalline urea, or other process streams consisting of a urea-containing aqueous solution. Among these process streams, the solution substantially composed of the aqueous urea solution obtained after separation of unreacted ammonia and ammonium carbamate from the urea synthesis effluent and the mother liquor from separation of crystalline urea are most preferable because they contain a larger amount of guanidine and are substantially free of ammonia and thus guanidine may be easily separated therefrom. The urea synthesis effluent or the aqueous urea solution generally contains 0.01–1% by weight of guanidine.

Guanidine in the urea synthesis effluent or in the aqueous urea solution is formed as a by-product chiefly in the urea synthesis zone or in the unreacted material separation zone wherein unreacted ammonia and ammonium carbamate are separated. The amount of the by-product depends on the reaction conditions of the urea production process, e.g., the temperature of the urea synthesis zone, the ammonia/carbon dioxide mole ratio, the water/carbon dioxide mole ratio, the conversion rate to urea, the temperature of the unreacted material separation zone, etc. For instance, in the urea production process operated at a temperature of 190°–200° C. under a pressure of 230–250 kg/cm$^2$ for an NH$_3$/CO$_2$ mole ratio of 4.1 and an H$_2$O/CO$_2$ mole ratio of 0.5, it has been found that the urea synthesis effluent discharged from the synthesis zone contains 0.01–0.05% by weight of guanidine. It has been also found that an aqueous urea solution obtained after separation of substantially all of unreacted ammonia and ammonium carbamate from the urea synthesis effluent contains 0.02–0.1% by weight of guanidine. Furthermore, the mother liquor which is obtained by concentrating the aqueous urea solution and separating crystalline urea contains 0.1–1% by weight of guanidine.

The guanidine content may further vary depending on conditions other than those mentioned above. For example, a combination of the urea process and a melamine process, use of an ammonia gas exhausted from other processes and withdrawal of the aqueous urea solution for another process will have an effect on the guanidine content in the process streams.

The separation of guanidine is suitably feasible by any of the known separation methods including, for example, an adsorption method, a method using a membrane, an extraction method, a crystallization method or a combination thereof. Needless to say, the separation according to the invention should not be construed as being limited to the above-mentioned methods.

Broadly speaking, the adsorption method can be classified into two categories, one category including the use of ion exchange resins, and the other category including the use of adsorbents such as activated carbon, silica gel, molecular sieves, etc.

In the adsorption method using ion exchange resins, either strongly or weakly acidic cation exchange resins may be used for the purpose. The amount of the ion exchange resin used depends on the concentration of guanidine in the solution to be treated, the amount of the solution fed and the feed time. Where it is desired to recover substantially all of the guanidine in solution, it is preferable to use the resin in an amount sufficient to have a greater exchange capacity than that required for the amount of guanidine to be recovered. If the solution from which guanidine is to be separated contains ammonia, the solution should preferably be contacted with the ion exchange resin in such an amount that the amount of quanidine contained therein is greater than the exchange capacity of the resin, thereby permitting substantially all of the ion exchange groups in the resin to adsorb guanidine. Then, the resin is subjected to elution to give highly pure guanidine which is substantially free of ammonia salt. In the latter case, guanidine and ammonia are both adsorbed on the exchange resin in the initial stage of the adsorption. However, since guanidine is adsorbed more selectively than ammonium ions, those ammonium ions which are adsorbed on the exchange resin will be in turn replaced by guanidine as the solution is passed continuously. Subsequently, guanidine alone is adsorbed on the resin.

The guanidine thus trapped on the ion exchange resin can be readily eluted by means of an aqueous acid solution. Though any acid (including mineral acids and organic acids) may be used for the above purpose, strong acids are generally used when the ion exchange resin employed is of the strongly acidic type. Either strong acids or weak acids may be used when the resin is of the weakly acidic type. Further, if it is desired to obtain guanidine hydrochloride, hydrochloric acid should preferably be used because the desired guanidine salt may be obtained in one step without further treatment. Similarly, if guanidine phosphate is required, phosphoric acid is preferably used. The acid should preferably be used in great excess for effective regeneration of the ion exchange resin and recovery of guanidine. In view of the purity of guanidine, however, it is preferable to employ the acid in an amount close to the equivalence of guanidine. Accordingly, the amount of the acid to be used depends upon the recovery percentage, purity, etc. The guanidine adsorbed on the exchange resin may also be eluted by use of aqueous solutions of salts or strong alkalies. When an aqueous solution of ammonium carbonate or ammonium hydrogencarbonate or an aqueous ammoniacal ammonium carbonate solution is used for the elution, guanidine is removed as guanidine carbonate, giving guanidine carbonate by a one stage treatment. The use of ammonium carbonate or ammonium hydrogencarbonate has a further advantage in that the ammonium carbonate or ammonium hydrogencarbonate used for the elution can be converted to and recovered as ammonia, water vapor and carbon dioxide and fed back to the urea synthesis process, making the production of guanidine carbonate very efficient. The ammonium carbonate or the ammonium hydrogencarbonate used for the elution can also be recovered as the respective salt and the recovered salt can be recycled for use in the elution step. The guanidine carbonate thus produced may be readily converted to any desired salt of guanidine by treatment with a corresponding strong acid.

The solution obtained by the elution contains several percent to several tens percent of a guanidine salt together with a small amount of ammonium salt and urea and an excess of the acid. If the ion exchange resin employed has a smaller adsorption selectivity to ammonia, the amount of the ammonium salt will be reduced correspondingly.

By concentrating the solution, crystals rich in the guanidine salt can be obtained. The crystals can be improved in purity by recrystallization or other means.

The separation method using membranes includes, for example, a reverse osmosis method or an electrodialysis method. In the reverse osmosis method, urea and ammonia tend to readily permeate through the reverse osmosis membrane. On the other hand, guanidine salts have a difficult time permeating through the membrane as do other salts in general, thus making the concentration of guanidine by the reverse osmosis method feasible. For instance, with a polyamide-base reverse osmosis membrane, the elimination rates for urea and ammonia are only less than 20%, and those for guanidine salts is as great as 80% or more. Use of such membranes facilitates the concentration of guanidine up to several percent while permitting urea and ammonia to selectively permeate through the membrane. After the concentration of guanidine, it is efficiently separated by means of any other method described herein.

Typical of the extraction method is a method wherein guanidine alone is extracted with a solvent immiscible with the aqueous urea solution. In another typical extraction method, a guanidine-containing solution is concentrated and evaporated to dryness, and then contacted with a solvent which is capable of dissolving urea but incapable of dissolving guanidine to remove urea alone by dissolution. Examples of solvents capable of extracting guanidine alone are phosphoric acid esters such as di-2-ethylhexyl phosphate. Of the solvents capable of dissolving urea alone, alcohols, such as methyl alcohol, are preferred. As described in Japanese Laid-open Publication No. 49-51225, liquid ammonia may be used for separating urea from guanidine salts by dissolving the urea.

In the crystallization method, a guanidine-containing solution is admixed with, for example, picric acid to precipitate guanidine as picrate. In this case, after separation of the guanidine salt, the remaining picric acid is removed from the solution by a suitable means.

The quanidine separated by any of the methods described above is very small in amount as compared with the amount of urea produced. However, the scale of urea production plants has recently become progressively larger. For example, some plants have a daily capacity of as great as 1000-1800 tons. At these capacities, the amount of separable guanidine will reach several hundred kilograms to several tons per day calculated as free guanidine. This enables separation of guanidine on an industrial scale.

As will be understood from the foregoing, guanidine can be prepared with ease and in safety, according to the process of the invention, by separating guanidine from the urea solution of a urea production plant.

The present invention will be particularly illustrated by way of the following examples, which should not be construed as limiting the present invention thereto.

EXAMPLE 1

Ammonia, carbon dioxide and an aqueous solution of recovered ammonium carbamate were reacted in a urea synthesis zone operated at a temperature of 195° C. and under a pressure of 250 kg/cm$^2$ (gauge) to give a urea synthesis effluent composed of urea, unreacted ammonia and ammonium carbamate, and water. The effluent was then treated in an unreacted material separation zone composed of three separation stages operated under 18 kg/cm$^2$ (gauge), 1.5 kg/cm$^2$ (gauge) and atmospheric pressure, respectively, thereby separating unreacted ammonia and ammonium carbamate from the effluent as a gaseous mixture of ammonia, carbon dioxide and water vapor. The resulting aqueous urea solution was concentrated in a crystallizer to precipitate crystalline urea, followed by melting and prilling. The three gaseous mixtures separated in the respective separation stages were absorbed in water or in an aqueous urea solution in three unreacted material recovering zones progressively, operated under substantially the same pressures as those of the separation stages respectively, and fed back to the urea synthesis zone. Part of the separated unreacted ammonia was cooled for condensation and also fed back to the urea synthesis zone. Part of the aqueous urea solution which was to be fed from the final stage of the unreacted material separation zone of the urea synthesis process to the crystallizing zone was passed to an apparatus, as shown in the FIGURE, packed with a cation exchange resin. The aqueous urea solution contained 0.05% by weight of guanidine. In the FIGURE, part of the aqueous urea solution was fed at a rate of 10 tons/hr through a pipe 1 and a valve 2 to an ion exchange resin-packed column 3. The column 3 was packed with 3000 of a weakly acidic cation exchange resin (having an ion exchange capacity of 4.5 meq/ml) by which substantially all guanidine contained in the solution was trapped. The resulting aqueous urea solution from which guanidine had been removed was fed back to the urea synthesis process through a valve 4 and a pipe 5.

To the column 3 was fed deionized water once a day, while stopping the feed of the aqueous urea solution, through a pipe 6 and a valve 7 to wash out urea remaining in the column. Then, about 900 l of a 10% hydrochloric acid solution was passed to the column through a pipe 11 and a valve 10 to regenerate the exchange resin. The discharged acid solution containing guanidine hydrochloride and hydrochloric acid was passed through a valve 9 and a pipe 8 to a guanidine-purifying and concentrating apparatus 14. Deionized water was again fed to the packed column 3 through the pipe 6 and valve 7 to wash out hydrochloric acid left in the column and discharged for reuse through a valve 12 and a pipe 13.

The apparatus 14 was heated under reduced pressure by means of a heater 15. The guanidine hydrochloride which had been concentrated into a slurry was fed through a pipe 16 to a centrifugal separator 17 and withdrawn from a pipe 18 in the form of crystalline guanidine hydrochloride. The mother liquor separated in the centrifugal separator 17 was fed back to the apparatus 14 through a pipe 19. Water and an excess of hydrochloric acid present were vaporized and passed through a pipe 20 to a vacuum generator 21. As a result, about 200 kg/day of the guanidine hydrochloride was obtained with a purity of about 90%.

EXAMPLE 2

In the crystallizing zone of the urea production process of Example 1, urea mother liquor obtained upon separation of crystalline urea by the centrifugal separator contained about 70% by weight of urea and about 0.2% by weight of guanidine. The urea mother liquor was passed at a rate of 2.5 tons/hr to the guanidine separating apparatus in the FIGURE in the same manner as in Example 1. Then, the trapped guanidine was recovered by the same procedure as in Example 1. As a result, guanidine hydrochloride with a purity of about 92% was obtained in an amount of about 200 kg/day.

EXAMPLE 3

When Example 1 was repeated using a urea synthesis process operated at 180° C. and a pressure of 200 kg/cm$^2$ (gauge), the urea mother liquor from the crystallizing zone obtained in the same manner as in Example 2 contained about 0.15% by weight of guanidine. The mother liquor was fed at a rate of 2 tons/hr to the guanidine separating apparatus in the FIGURE in the same manner as in Example 1 or 2 using 950 l of a 10% nitric acid solution instead of 10% hydrochloric acid. As a result, about 155 kg/day of guanidine nitrate with a purity of 91% was obtained.

EXAMPLE 4

In Example 1, the column 3 was packed with 1000 l of methaacrylic acid type weakly acidic ion exchanger resin (having an ion exchange capacity of 3 meq./ml), which is prior to the passage of the aqueous urea solution, aqueous ammonia was fed to the column in an amount sufficient to convert the ion exchange resin to an ammonium salt form. Then, the aqueous urea solution was fed to the column and guanidine was adsorbed on the resin. Instead of regenerating the resin by passing thereto 10% hydrochloric acid from the pipe 11 and the valve 10, 1678 l of an aqueous ammonium carbonate solution containing 200 g/l of ammonium carbonate and 75 g/l of ammonia was passed to the column to elute guanidine and simultaneously to regenerate the resin in an ammonium salt form. Then, 500 l of deionized water was added through pipe 10 and valve 11 to wash out residual solution in column 3. As a result, there was obtained 2256 kg of an aqueous solution containing 7.4% by weight of guanidine carbonate, 10.9% by weight of ammonium carbonate, and 5.6% weight of ammonia. The aqueous solution was fed through the pipe 8 to the guanidine carbonate crystallizing apparatus wherein it was concentrated and centrifugally separated to give crystalline guanidine carbonate. The amount of crystals obtained were 170 kg/day. These crystals were composed of 97.0% by weight of guanidine carbonate, 0.2% by weight of ammonium carbonate, 2.5% by weight of water and 0.3% by weight of other impurities. The crystals were dried to obtain guanidine carbonate with a purity of 99.5% or more.

The gas generated and separated in the crystallizing step and drying step and containing ammonia, carbon dioxide and water vapor was recovered and fed back to the unreacted material recovering step of the urea synthesis process.

EXAMPLE 5

The urea mother liquor as obtained in Example 2 was fed to a reverse osmosis apparatus using a polyamide-base reverse osmosis membrane having an area of 88 m$^2$ at a feed rate of 132 l/hr under an input pressure of 40 kg/cm$^2$. The concentrated solution was taken out at a rate of 8.2 l/hr while the permeated solution was obtained in 123.8 l/hr. The permeated solution was fed back to the urea production process.

The concentrated solution contained about 72% by weight of urea and 3.2% by weight of guanidine. Eighteen kg of the guanidine-rich aqueous urea solution thus obtained was then admixed with 5 kg of 10% phosphoric acid and sufficiently stirred, followed by evaporation of the water at a temperature of 80° C. under reduced pressure to obtain about 14 kg of crystals. To the crystals was added 21 kg of methanol, which was then heated to 60° C. to dissolve most of the crystals. The remaining solid matters insoluble in methanol were collected by filtration to give 930 g of crystalline diguanidine phosphate with a purity of 91%. The filtrate which consisted of a methanol solution of urea was subjected to evaporation to remove methanol therefrom, thereby recovering urea and methanol. The thus recovered urea had the same quality as powdery urea obtained in conventional urea production processes.

EXAMPLE 6

Two kg of the urea mother liquor as produced in Example 2 was added with 300 ml of an n-heptane solution containing 120 ml of di-2-ethylhexyl phosphate. The mixture was sufficiently agitated and allowed to stand until it separated into an aqueous phase (1) and an organic phase (2). To the organic phase (2) was added 100 ml of 5% sulfuric acid, which was then sufficiently agitated and allowed to stand until it separated into an aqueous phase (3) and an organic phase (4). The aqueous phase (3) thus obtained was then admixed with an aqueous barium oxide solution to adjust its pH to 6.5. The resultant precipitate of barium sulfate was removed by filtration and the filtrate was subjected to evaporation of water to obtain 6.2 g of guanidine sulfate with a purity of 95%. The separated organic phase (4) was found to be composed of an n-heptane solution of di-2-ethylhexyl phosphate in a regenerated state and was reusable. The aqueous phase (1) was found to be composed of an aqueous urea solution and fed back to the urea production process for recovery.

What is claimed is:

1. A process for preparing guanidine, comprising separating guanidine from a process stream derived from a urea production process in which ammonia and carbon dioxide are reacted under high temperature and high pressure conditions to give urea, said guanidine being a by-product produced in the urea synthesis.

2. A process as claimed in claim 1, wherein the process stream is a solution obtained after separation of unreacted ammonia and ammonium carbamate from the urea synthesis effluent from a urea synthesis zone in the urea production process.

3. A process as claimed in claim 1, wherein the process stream is a mother liquor obtained in the urea production process by separating unreacted ammonia and ammonium carbamate from urea synthesis effluent from the urea synthesis zone, concentrating the resulting aqueous urea solution and separating crystalline urea from said urea solution.

4. A process as claimed in claim 1, further comprising recycling the process stream obtained after the separation of guanidine to the urea production process.

5. A process as claimed in claim 1, wherein the separation step includes adsorbing guanidine on an ion exchange resin and recovering guanidine therefrom by elution.

6. A process as claimed in claim 5, wherein said ion exchange resin is a cation exchange resin.

7. A process as claimed in claim 6, wherein the elution of guanidine is effected with an acid.

8. A process as claimed in claim 6, wherein the elution of guanidine is effected with an aqueous solution of a salt or salts.

9. A process as claimed in claim 8, wherein said aqueous solution is a solution of ammonium carbonate and/or ammonium hydrogencarbonate or an ammoniacal ammonium carbonate solution.

10. A process as claimed in claim 9, further comprising recovering the ammonium carbonate, ammonium hydrogencarbonate or ammonia employed for the elution of guanidine as a gaseous mixture comprising carbon dioxide and ammonia and feeding the recovered gaseous mixture to a step in the urea production process where unreacted materials are recovered.

11. A process as claimed in claim 1, wherein guanidine is separated after being concentrated by a reverse osmosis method.

12. A process as claimed in claim 11, wherein a polyamide-base reverse osmosis membrane is used.

13. A process as claimed in claim 1, wherein the separation of guanidine is effected by extraction with a phosphoric acid ester.

14. A process as claimed in claim 13, wherein said ester is di-2-ethylhexyl phosphate.

15. A process as claimed in claim 11, wherein the separation of guanidine is conducted by evaporating the aqueous solution containing guanidine and urea to dryness after concentration of guanidine, dissolving the urea in a solvent capable of selectively dissolving urea, and collecting the remaining guanidine.

16. A process as claimed in claim 15, wherein said solvent is an alcohol or liquid ammonia.

17. A process as claimed in claim 1, wherein guanidine is separated as a precipitate of picrate thereof.

18. A process as claimed in claim 9, further comprising recovering the ammonium carbonate or ammonium hydrogencarbonate employed for the elution of guanidine as a salt and recycling the recovered salt to the elution step.

19. A process as claimed in claim 9, wherein said cation exchange resin is converted to ammonium salt form prior to passage of said process stream.

* * * * *